(12) United States Patent
Avlund

(10) Patent No.: US 8,915,887 B2
(45) Date of Patent: Dec. 23, 2014

(54) MEDICAL INJECTION DEVICE WITH LARGE, MECHANICAL CIPHER DOSE DISPLAY

(75) Inventor: Mikkel Avlund, Soeborg (DK)

(73) Assignee: Novo Nordisk A/S, Bagsvaerd (DK)

( * ) Notice: Subject to any disclaimer, the term of this patent is extended or adjusted under 35 U.S.C. 154(b) by 0 days.

(21) Appl. No.: 14/008,802

(22) PCT Filed: Mar. 29, 2012

(86) PCT No.: PCT/EP2012/055710
§ 371 (c)(1),
(2), (4) Date: Sep. 30, 2013

(87) PCT Pub. No.: WO2012/130991
PCT Pub. Date: Oct. 4, 2012

(65) Prior Publication Data
US 2014/0052068 A1 Feb. 20, 2014

Related U.S. Application Data

(60) Provisional application No. 61/472,477, filed on Apr. 6, 2011.

(30) Foreign Application Priority Data

Mar. 31, 2011 (EP) .................................... 11160635

(51) Int. Cl.
| | |
|---|---|
| A61M 5/00 | (2006.01) |
| G09F 9/37 | (2006.01) |
| A61M 5/20 | (2006.01) |
| A61M 5/24 | (2006.01) |
| A61M 5/315 | (2006.01) |
| A61M 5/31 | (2006.01) |

(52) U.S. Cl.
CPC .. *A61M 5/24* (2013.01); *G09F 9/37* (2013.01); *A61M 5/31553* (2013.01); *A61M 5/20* (2013.01); *A61M 2005/3126* (2013.01); *A61M 5/31546* (2013.01); *A61M 2005/3125* (2013.01)
USPC ........................................................ 604/207

(58) Field of Classification Search
CPC ................... A61M 5/3155; A61M 2005/3123; A61M 2005/3125
USPC .................. 604/181, 186, 187, 189, 207–211
See application file for complete search history.

(56) References Cited

U.S. PATENT DOCUMENTS

| | | | |
|---|---|---|---|
| 3,683,523 | A | 8/1972 | Boyles |
| 3,977,179 | A | 8/1976 | Bachmann |
| 6,235,004 | B1 | 5/2001 | Steenfeldt-Jensen et al. |

FOREIGN PATENT DOCUMENTS

| | | |
|---|---|---|
| DE | 2629224 A1 | 12/1977 |
| DE | 102004063649 A1 | 7/2006 |

(Continued)

*Primary Examiner* — Theodore Stigell
*Assistant Examiner* — Amber Stiles
(74) *Attorney, Agent, or Firm* — Wesley A. Nicolas; Reza Green; Richard W. Bork

(57) ABSTRACT

An injection device is disclosed which comprises a housing (10) with a display for showing the size of a set dose. The display is formed from a number of individual ciphers (11, 40) which each comprises a plurality of segments (13, 14) extending horizontally and vertically. At the end of the injection device a dose setting element (20) is provided for allowing the user to set the size of the dose to be injected. Further, the display mechanism comprises a first pattern (35) for showing the vertical segments (14), and a second pattern (25) for showing the horizontal segments (13). The patterns (25, 35) are associated with the dose setting button (20) and arranged to be moved when the dose setting button (20) is operated. The injection device disclosed can have any number of ciphers (11, 40) which is coupled to each other in order to show to the user the size of any dose set.

6 Claims, 5 Drawing Sheets

(56) References Cited

FOREIGN PATENT DOCUMENTS

| | | |
|---|---|---|
| EP | 758122 A1 | 2/1997 |
| FR | 2882162 A1 | 8/2006 |
| JP | 51102599 | 9/1976 |
| WO | 01/87386 A1 | 11/2001 |
| WO | 2006/045528 | 5/2006 |
| WO | 2009/070911 A1 | 6/2009 |

MEDICAL INJECTION DEVICE WITH LARGE, MECHANICAL CIPHER DOSE DISPLAY

CROSS-REFERENCE TO RELATED APPLICATIONS

This application is a 35 U.S.C. §371 National Stage application of International Application PCT/EP2012/055710 (published as WO 2012/130991), filed Mar. 29, 2012, which claimed priority of European Patent Application 11160635.6, filed Mar. 31, 2011; this application claims priority under 35 U.S.C. §119 of U.S. Provisional Application 61/472,477; filed Apr. 6, 2011.

THE TECHNICAL FIELD OF THE INVENTION

The invention relates to an injection device with a large display and especially an injection device with the ability to display the dose setting size in large ciphers.

DESCRIPTION OF RELATED ART

Many known injection devices and especially pen shaped injection devices have a limited space for the ciphers displaying the dose set by the user.

U.S. Pat. No. 6,235,004 disclose a pen shaped injection where the ciphers are printed on a scale drum which passes a window in the housing as the dose is set. It gives itself that there is a very limited space available for the ciphers on the scale drum.

Such construction makes it difficult for the user to properly identify the ciphers if the patient e.g. has reduced sight, which is not uncommon for people suffering from diabetic complications.

For mechanical signs such as price indicators it is known to design each cipher from a plurality of segments as in a digital electronic display. These ciphers are often, as e.g. disclosed in EP 758,122 formed from 4 vertical segments and 3 horizontal segments. By indicating the relevant bars of segments the ciphers from 0 to 9 can displayed.

A similar mechanical digital display is disclosed in U.S. Pat. No. 3,683,523. Here the segments are carved out in a front plate. The patterns forming the segments are disposed on 2 plates that are simultaneously moved behind the front plate. The horizontal bars are disposed on a plate moved vertically and the vertical bars are disposed on a different plate which is moved horizontally. A further mechanical digital display is disclosed in JP Utility model No.: 51-102599.

DESCRIPTION OF THE INVENTION

It is an object of the present invention to provide an injection device in which the size of the individual ciphers indicating the set dose can be increased to enhance visibility. It is further an object to provide large ciphers suitable to be implemented in a mechanical pen shaped injection device.

The invention is defined in claim 1.

Accordingly, the injection device is the type in which a liquid drug such as insulin or the like is injected from a cartridge contained in the injection device via a needle cannula of a needle assembly and into the body of a patient.

In order to visible inspect the size of the dose set by the user a display comprising a number of individual ciphers is provided in the housing of the injection device.

Each of the ciphers is formed by a plurality of segments which are carved out or otherwise provided in the housing of the injection device. Normally to form a digital cipher, three segments extend horizontally and four segments extend vertically. However, other number of segments are possible. Two different patterns are provided which have a number of coloured bars. These bars blocks out the segments to form the ciphers from "0" to "9". A first pattern is arranged to block out the vertical segments and a second pattern is arranged to block out the horizontal segments. However, other combinations of patterns are possible. The first and the second pattern are arranged such that they move when the user operates the injection button. The patterns preferably move in a direction perpendicular to each other, one pattern moves horizontally and the other pattern moves vertically. Together the coloured bars of the two patterns block out the segments in numerical order to indicated the incremental setting of the dose size.

As dose setting buttons are usually rotated during dose setting, the first pattern and the second pattern associated with the dose setting button also rotates during dose setting.

The dose setting element is guided in a groove provided on the inside peripheral surface of the housing. The groove or track is preferably circular such that the injection button does not move axially out of the injection device during dose setting. Such embodiment is particular suitable for an automatic injection device where the rotation of the injection button tightens a spring which later delivers the force used for performing the injection.

The pattern blocking out the horizontal segments are attached to the injection button such that the coloured bars passes the horizontal segments as the injection button is rotated. The coloured bars are preferably printed on a thin transparent sheet made from a suitable polymer.

Further, a guide sleeve is provided which rotates with the dose setting element but is axially guided in the housing such that it moves axially during its rotation. The axial movement of the guide sleeve is preferably controlled by a cam-shaped track provided on the peripheral inside surface of the housing.

The pattern blocking out the vertical segments are coupled to the guide member such that this first pattern moves axially relatively to the vertical segments when the dose setting element is rotated.

The ciphers can be arranged perpendicular to the longitudinal extension of the pen shaped injection device, or the ciphers can be arranged in a direction aligned in parallel with the longitudinal extension. When the ciphers are aligned with the longitudinal direction, the injection device is equally suitable both for right handed and for left handed persons.

The present invention is suitable for showing any number of ciphers. The ciphers are coupled together by a coupling mechanism which operates the most left cipher one incremental position following each ten incremental position of the cipher right to the most left cipher. Such that when the last cipher changes from "9" to "0", the cipher to the left is changed one position.

The coupling mechanism comprises an additional guide member which performs an axial movement as a result of the rotational movement of the dose setting element. The additional guide member is guided in a cam-track provided on an inside surface of the housing and which cam shape moves the additional guide member axially whenever the cipher to the left is to be changed. In order to rotate the patterns controlling the next cipher, an intermediate member is provided which rotates when the additional guide member is shifted axially and rotated.

In a further embodiment the invention relates to a display mechanism for an injection device, which display mechanism is formed by a number of ciphers each comprising a plurality of segments, a number of which segments extend predominantly horizontally and a number of which segments extent predominantly vertically, like in a digital number.

A rotatable dose setting element which allows the user to set the size of the dose to be injected by rotation is further provided. The rotatable dose setting element is preferably guided in a circular track such that the dose setting element does not move axially during rotation.

The vertical segments (or bars) form a first pattern and the horizontal segments (or bars) form a second pattern. These patterns can be moved in relation to each other in and out of contact with the segments which are preferably provided in a housing to form "digital" ciphers. The segments are preferably formed as cut-outs in the housing forming the injection device and the patterns forming the horizontal and vertical segments, bars or bands are moved below or behind the cut-out segments. The combination of filled-out and not filled-out horizontal and vertical segments generates the image of a "digital" cipher.

In a tubular injection device, one of the first or second patterns are preferably coupled to the rotatable dose setting button, and the other of the first or second patterns are coupled to a guide sleeve provided internally in the injection device.

The guide sleeve is rotatable coupled to the dose setting member such that they rotate together. In addition, the guide sleeve is guided in an internal track in the housing of the injection device.

This guide track is preferably formed such that the guide sleeve oscillates axially when rotated in order to bring the vertical segment of the first pattern in and out of contact with the vertical segments which is preferably formed in the housing.

Further the dose setting element and the guide member is formed as hollow tubular elements, or at least tubular elements, rotatable mounted in a housing where the rotatable dose setting member extend internally in the hollow and tubular guide member and is coupled to the guide member such that the two element rotate together. The rotatable engagement between the rotatable dose setting member and the rotatable guide sleeve can e.g. be a tongue and groove connection; however other connections could also be used.

DEFINITIONS

An "injection pen" is typically an injection apparatus having an oblong or elongated shape somewhat like a fountain pen for writing. Although such pens usually have a tubular cross-section, they could easily have a different cross-section such as triangular, rectangular or square or any variation around these geometries.

As used herein, the term "drug" is meant to encompass any drug-containing flowable medicine capable of being passed through a delivery means such as a hollow needle in a controlled manner, such as a liquid, solution, gel or fine suspension. Representative drugs includes pharmaceuticals such as peptides, proteins (e.g. insulin, insulin analogues and C-peptide), and hormones, biologically derived or active agents, hormonal and gene based agents, nutritional formulas and other substances in both solid (dispensed) or liquid form.

Correspondingly, the term "subcutaneous" injection is meant to encompass any method of transcutaneous delivery to a subject.

Further the term "injection needle" defines a piercing member adapted to penetrate the skin of a subject for the purpose of delivering or removing a liquid.

The term "Needle Cannula" is used to describe the actual conduit performing the penetration of the skin during injection. A needle cannula is usually made from a metallic material and connected to a hub to form an injection needle. A needle cannula could however also be made from a polymeric material or a glass material. The hub which carries the connecting means for connecting the injection needle to an injection apparatus is usually moulded from a suitable thermoplastic material.

"Cartridge" is the term used to describe the container containing the drug. Cartridges are usually made from glass but could also be moulded from any suitable polymer. A cartridge or ampoule is preferably sealed at one end by a pierceable membrane which can be pierced e.g. by an injection needle. The opposite end is closed by a plunger or piston made from rubber or a suitable polymer. The plunger or piston can be slidable moved inside the cartridge. The space between the pierceable membrane and the movable plunger holds the drug which is pressed out as the plunger decreased the volume of the space holding the drug.

All references, including publications, patent applications, and patents, cited herein are incorporated by reference in their entirety and to the same extent as if each reference were individually and specifically indicated to be incorporated by reference and were set forth in its entirety herein.

All headings and sub-headings are used herein for convenience only and should not be constructed as limiting the invention in any way.

The use of any and all examples, or exemplary language (e.g. such as) provided herein, is intended merely to better illuminate the invention and does not pose a limitation on the scope of the invention unless otherwise claimed. No language in the specification should be construed as indicating any non-claimed element as essential to the practice of the invention.

The citation and incorporation of patent documents herein is done for convenience only and does not reflect any view of the validity, patentability, and/or enforceability of such patent documents.

This invention includes all modifications and equivalents of the subject matter recited in the claims appended hereto as permitted by applicable law.

BRIEF DESCRIPTION OF THE DRAWINGS

The invention will be explained more fully below in connection with a preferred embodiment and with reference to the drawings in which.

The figures are schematic and simplified for clarity, and they just show details, which are essential to the understanding of the invention, while other details are left out. Throughout, the same reference numerals are used for identical or corresponding parts.

DETAILED DESCRIPTION OF EMBODIMENT

When in the following terms as "upper" and "lower", "right" and "left", "horizontal" and "vertical", "clockwise" and "counter clockwise" or similar relative expressions are used, these only refer to the appended figures and not to an actual situation of use. The shown figures are schematic representations for which reason the configuration of the different structures as well as there relative dimensions are intended to serve illustrative purposes only.

In that context it may be convenient to define that the term "distal end" in the appended figures is meant to refer to the end of the injection device carrying the injection needle whereas the term "proximal end" is meant to refer to the opposite end pointing away from the injection needle.

Figure 1:
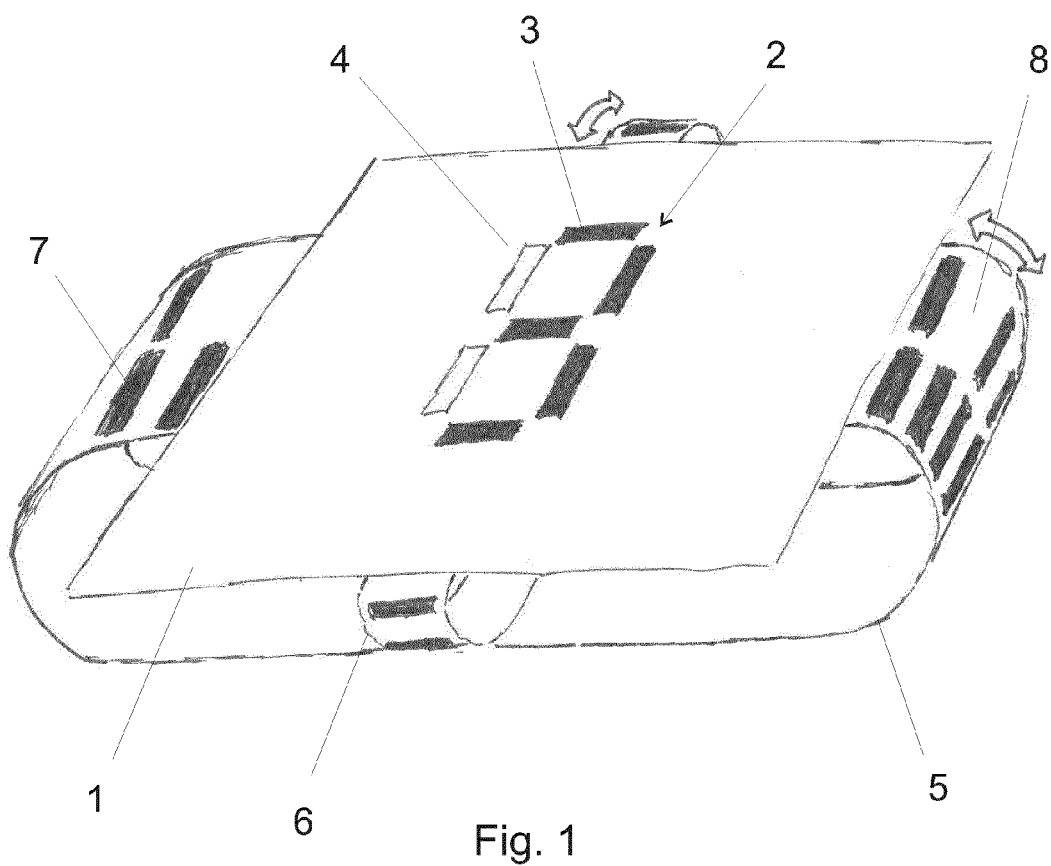
FIG. 1 Show the principle of forming the ciphers.

FIG. 1 discloses the principle of forming the individual ciphers. A front plate 1 is provided with seven segments 2 carved out. The segments 2 could alternatively be provided as transparent areas in the front plate 1. Three horizontal segments 3 of the seven segments 2 extend horizontally and the other four vertical segments 4 of the seven segments 2 extend vertically. A first band 5 carrying a specific vertical pattern is moved in the horizontal direction pass the vertical segments 4 and a second band 6 carrying a specific horizontal pattern is moved vertically pass the horizontal segments 2. The patterns are made from a plurality of coloured bars 7 separated by white or opaque areas 8. In FIG. 1, the bands 5, 6 are in a relative position where the two most right of the vertical segments 4 and all three of the horizontal segments 3 are blocked out by coloured bars 7 thereby forming the cipher "3".

The combination between the movement of the two bands (5, 6) and thus the pattern printed on the bands produces the ciphers from "0" to "9".

Figure 2:
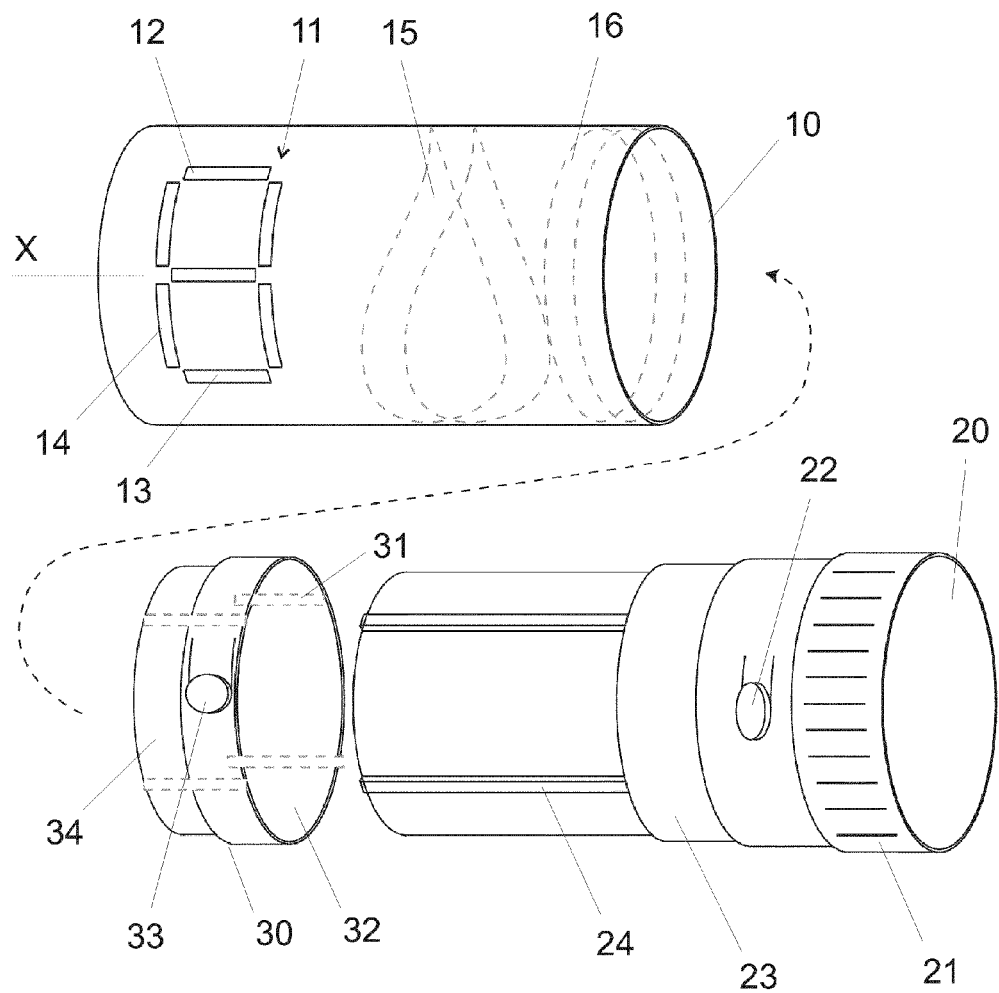
FIG. 2 Show an exploded view of an injection device having one cipher.

FIG. 2 discloses the dose setting mechanism of a pen shaped injection device in which one cipher 11 is provided extending perpendicular to the longitudinal axis X of the pen shaped injection device. A housing 10 is provided with a cipher 11 formed from seven carved out segments 12. The seven segments 12 are composed of three horizontal segments 13 and four vertical segments 14. The inside surface of the housing 10 is provided with two different tracks 15, 16. The first track 15 form a specific cam pattern 17 (see FIG. 3B) and extend on the inside periphery of the housing 10. The second track 16 extend circular around the inside periphery of the housing 10.

At the proximal end of the housing 10, a dose setting member 20 is provided. This dose setting member 20 has a finger part 21 which can be gripped by the user when setting a dose. Further, it has a protrusion 22 engaging the second track 16 of the housing 10 such that the dose setting member 20 can rotate relatively to the housing 10 but not move axially relatively to the housing 10. The dose setting member 20 is also provided with an outer surface 23 carrying the horizontal pattern 25 such that when the injection button 20 is rotated, the horizontal pattern 25 passes the horizontal segments 13 thereby forming the horizontal part of the cipher 11. The horizontal pattern 25 which is disclosed in FIG. 3C can be printed on an opaque polymeric second film 26 which is secured to the outer surface 23 of the injection button 20. The second film 26 carrying the horizontal pattern 25 can extend beyond the outer surface 23 as long as it rotates together with the injection button 20.

Further, the dose setting member 20 is provided with a number of axially raised bars 24 which engages similar tracks 31 on the inside surface 32 of a guide sleeve 30. The position of the raised bars 24 and the tracks 31 are insignificant, what matters is that the dose setting member 20 and the guide sleeve 30 rotate together but can move axially relatively to each other.

The guide sleeve 30 is further provided with a cam protrusion 33 guided in the first track 15 of the housing 10. The guide sleeve 30 is forced to rotate when the dose setting member 20 is rotated due to engagement between raised bars 24 and the tracks 31, at the same time the guide sleeve 30 is forced to follow the cam pattern 17 of the first track 15. The guide sleeve 30 is provided with an outside surface 34 carrying the vertical pattern 35 (see FIG. 3A) such that the axial movement of the guide sleeve 30 provides for the vertical part 14 of the cipher 11. The vertical pattern 35 is preferably printed on an opaque polymeric first film 36 which is coupled to the outside surface 34 of the guide sleeve 30 such that the vertical pattern 35 is shifted in the axial direction as the cam protrusion 33 moves in regard of the cam pattern 17 of the first track 15.

Figure 3A:
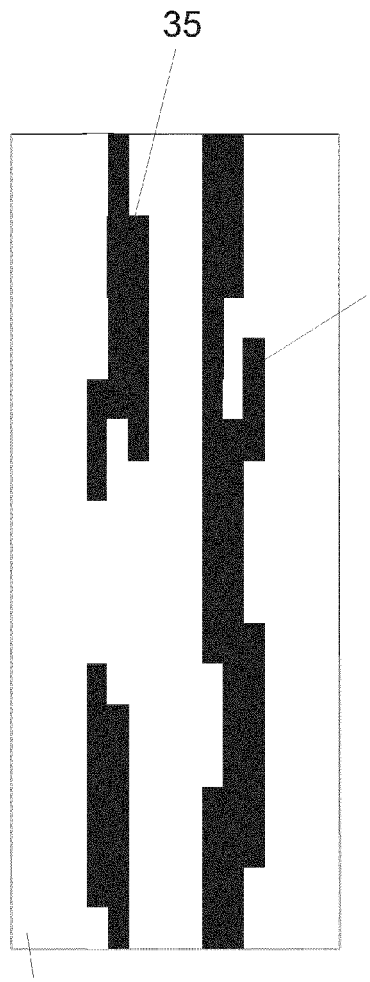
FIG. 3A+C Show the patterns used for forming the cipher of FIG. 2.
Figure 3B:
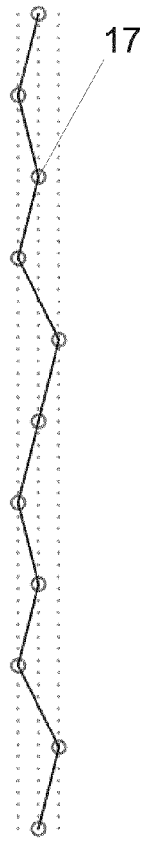
FIG. 3B Show the lay-out of the cam track of the injection device of FIG. 2.
Figure 3C:
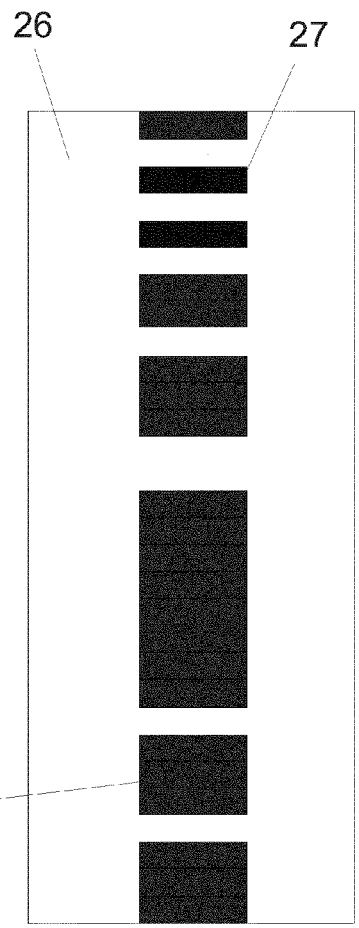

FIG. 3A-C discloses the different pattern used in connection with the embodiment of FIG. 2. FIG. 3A discloses the first pattern 35 which is visible through the vertical segments 14. The first pattern 35 is printed on a thin opaque polymeric first film 36 and attached to the guide sleeve 30. As the guide sleeve 30 is guided in the cam pattern 17 as disclosed in FIG. 3B, the coloured bars 37 making up the first pattern 35 are axially shifted in and out of the vertical segments 14.

At the same time, the dose setting member 20 is rotated thereby bringing the coloured bars 27 of the second pattern 25 in and out of the horizontal segments 13. The second pattern 25 is disclosed in FIG. 3C is also printed on an opaque second film 26 which is attached to the dose setting member 20. Due to the opaqueness of the films 26, 36 it is possible to e.g. view the coloured bars 27 of the second film 26 through the first film 36 (and vice versa).

Figure 4:
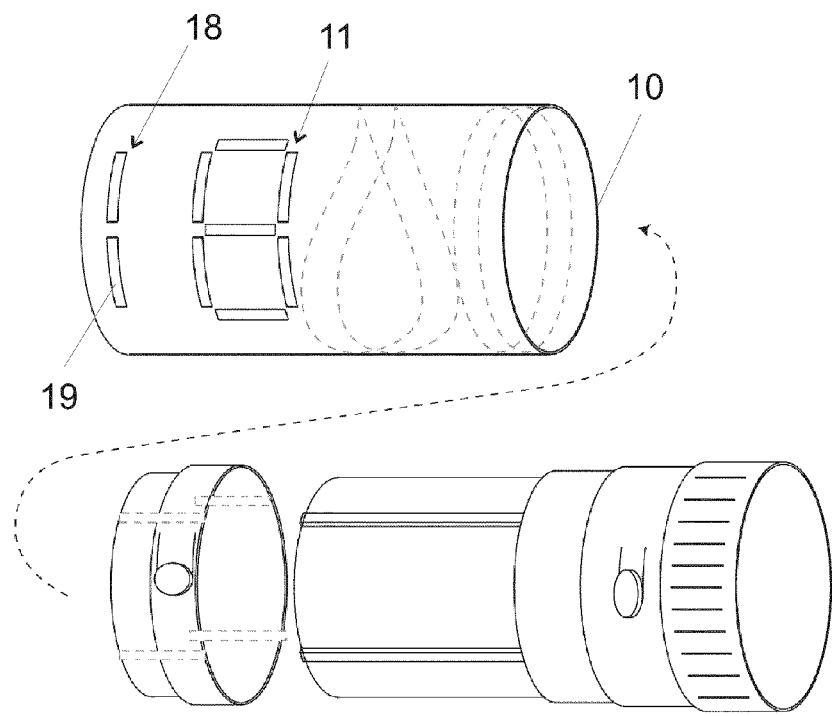
FIG. 4 Show a different example of the injection device of FIG. 2.

FIG. 4 discloses an embodiment in which a second cipher 18 made up from only two vertical segments 19 have been added. This cipher 18 can only show "1" or nothing. By adding an additional column of not disclosed coloured bars to the first film 36 which additional column is shifted axially in and out of the segments 19 this second cipher 18 can be controlled such that the injection device can show the ciphers from "0" to "19".

Figure 5:
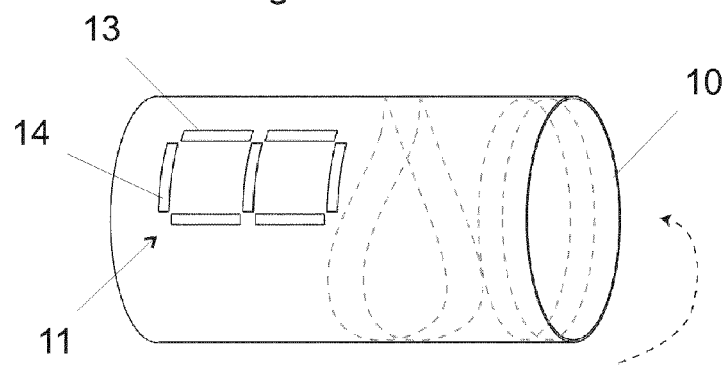
FIG. 5 Show another example of the injection device of FIG. 2.

FIG. 5 discloses an embodiment in which the cipher 11 has been arranged in parallel with the longitudinal axis X of the housing 10 of the pen shaped injection device. The cipher 11 disclosed in FIG. 5 has four horizontal segments 13 and three vertical segments 14. The patterns 25, 35 of the opaque films 26, 36 must be altered to accommodate this.

If the ciphers are arranged in parallel with the longitudinal axis X of the housing, it will be easier for left-handed people to read the ciphers. Injections pens are normally designed for right-handed people, however US 2009/0264828 suggest to invert the ciphers on an ordinary scale drum in order to make an injection pen dedicated for left-handed users. However, by arranging the ciphers as suggested here, the same injection pen is equally suitable for left-handed and for right-handed persons. The general idea of arranging the ciphers in parallel with the housing can also be implemented in injection pens having a scale drum as the ones disclosed in U.S. Pat. No. 6,235,004 and in US 2009/0264828.

Figure 6A:
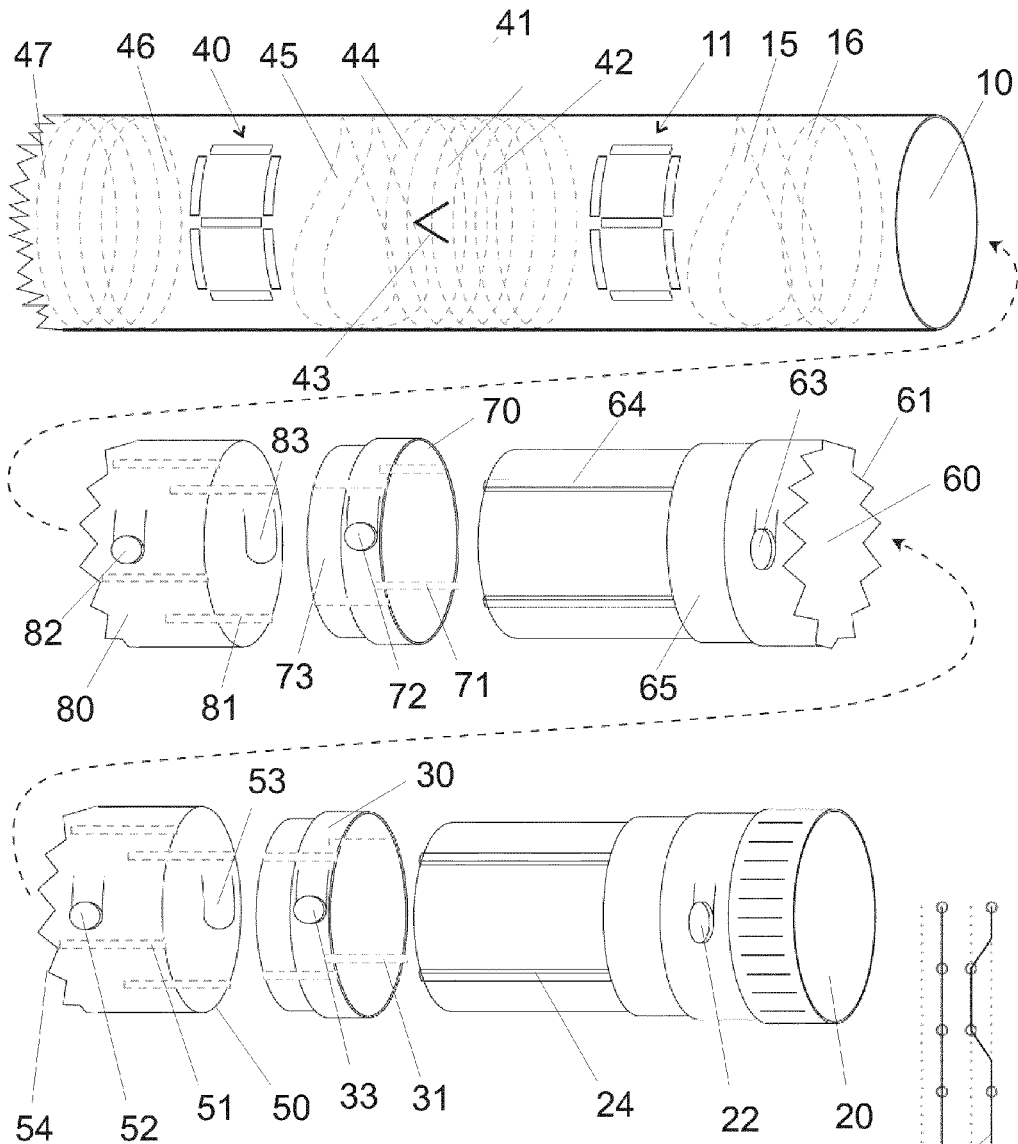
FIG. 6A Show an injection device with several ciphers.
Figure 6B:
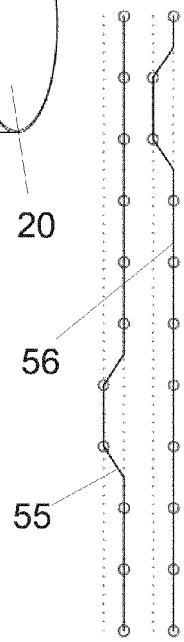
FIG. 6B Show the lay-out of the cam track of the injection device of FIG. 6A.

FIG. 6 discloses an embodiment in which any number of ciphers can be shown. As discloses in FIG. 2, a guide member 30 is guided in a first track 15 and rotational coupled to a dose setting member 20. The dose setting member 20 is guided in the second track 16. The dose setting member 20 and the guide member 30 drives the patterns making up the helical and the vertical bars of the first cipher 11. In addition to this a further cipher 40 is provided as here explained thus making it possible to display ciphers up to "99".

A second guide member 50 is also coupled to the dose setting button 20 by having a number of tracks 51 engaging the raised bars 24 of the dose setting member 20. In this way the second guide member 50 rotate together with the dose setting member 20 but can move axially relatively to the dose setting member 20. The second guide member 50 is provided with two protrusions 52, 53 which is guided in tracks 41, 42 provided on an inside surface of the housing 10.

The tracks 41, 42 has a cam shape 55, 56 (see FIG. 6B) such that the second guide member 50 is moved axially once for each tenth incremental position of the dose setting member 20, meaning that each time the cipher "9" has been shown and the first cipher 11 returns to its zero showing, the second guide member 50 is moved axially.

The second guide member 50 is at its distal end provided with a number of V-shaped teeth 54 which engages a corresponding set of proximal pointing teeth 61 provided on an intermediate member 60 every time the second guide member 50 is moved axially. When the second guide member 50 is moved axially and rotated in its axial position it brings the intermediate member 60 with it, however as the cam shape 55, 56 shows, the intermediate member 60 is only rotated once for each tenth incremental position of the second guide member 50.

The intermediate member 60 is further provided with a protrusion 63 guided in a circular, peripheral track 44 provided in the housing, limiting the movement of the intermediate member 60 to purely rotational.

Further, the proximal pointing teeth 61 of the intermediate member 60 is locked by a locking member 43 provided on the inside surface of the housing 10. This locking element 43 is V-shaped and engages the proximal pointing teeth 61 of the intermediate member 60 preventing the intermediate member 60 from rotating. When the second guide member 50 is moved axially it releases the locking element 43 thereby setting the intermediate member 60 free to rotate with the second guide member 50 until the guide member 50 is axially moved back to its initial position whereby the locking element 43 again engages the proximal pointing teeth 61.

The intermediate member 60 is provided with a raised bar 64 engaging longitudinal tracks 71 provided in a third guide member 70 such that this third guided member 70 rotates with the intermediate member 60 but can move axially relatively to the intermediate member 60.

The third guide member 70 is further provided with a protrusion 72 which is guided in a track 45 in the housing which track 45 is cam shaped such that the third guide member 70 is moved axially when rotated.

The intermediate member 60 has an outer surface 65 to which a pattern controlling the horizontal segments of the second cipher 40 is attached and the third guide member 70 has an outer surface 73 to which another pattern is attached controlling the vertical segments of the second cipher 40.

The different tracks 41, 42, 44, 45 can be provided in other positions if needed, e.g. such that the first cipher 11 and the second cipher 40 can be brought closer to each other. Further two vertical segments can be added and controlled by an additional column of coloured bars provided on the third guide member 70 such as to change the two vertical segments between displaying nothing and displaying "1" as previously explained. In this way ciphers up to "199" can be displayed.

A fourth guide member 80 having longitudinal tracks 81 can further be connected to the intermediate member 60 in order to control yet a mechanism for a not shown third cipher. This fourth guide member 80 is provided with two protrusions 82, 83 which are guided in two cam tracks 46, 47 provided in the housing 10. As with the second guide member 50, the fourth guide member 80 moves axially for each tenth incremental position of intermediate member 60 such that the third cipher is changed one increment for each ten increments change of the second cipher 40.

Some preferred embodiments have been shown in the foregoing, but it should be stressed that the invention is not limited to these, but may be embodied in other ways within the subject matter defined in the following claims.

The invention claimed is:

1. An injection device comprising:
A housing having a display for showing the size of a set dose, the display being formed by a number of ciphers each comprising a plurality of segments, a number of which segments extend predominantly horizontally and a number of which segments extend predominantly vertically,
A rotatable dose setting element for allowing the user to set the size of the dose to be injected, and wherein a second pattern of bars associated with the horizontal segments is coupled to the dose setting element,
a guide sleeve rotatably coupled to the dose setting element such that the guide sleeve rotates together with the dose setting element, and wherein a first pattern of bars associated with the vertical segments, is coupled to the guide sleeve,
wherein the first pattern of bars and the second pattern of bars are functionally associated with the dose setting element and arranged to be moved when the dose setting element is operated, and wherein;
dose setting element is guided in a second track provided on an interior surface of the housing, the second track is a circular track extending peripheral around the inside surface of the housing, and
the guide sleeve is axially guided in a first track provided on an interior surface of the housing, the first track being a cam-shaped track extending peripheral around the inside surface of the housing.

2. An injection device according to claim 1, wherein ciphers are aligned to extend in parallel with a longitudinal axis of the injection device.

3. An injection device according to claim 2, wherein a coupling mechanism is provided which couples the first cipher to a further cipher.

4. An injection device according to claim 3, wherein the coupling mechanism comprises an additional guide member which perform an axial movement as a result of the rotational movement of the dose setting member.

5. An injection device according to claim 4, wherein the additional guide member is guided in a track following a specific cam peripheral provided on the inside surface of the housing for controlling the axial movement of the additional guide member.

6. An injection device according to claim 4, wherein the additional guide member releases a locking mechanism to drive an intermediate member controlling the second cipher.

* * * * *